United States Patent [19]

Seligson et al.

[11] Patent Number: 4,935,342

[45] Date of Patent: Jun. 19, 1990

[54] METHOD OF ISOLATING AND PURIFYING NUCLEIC ACIDS FROM BIOLOGICAL SAMPLES

[75] Inventors: David B. Seligson, Wauwatosa, Wis.; Elsie J. Shrawder, San Diego, Calif.

[73] Assignee: Syngene, Inc., San Diego, Calif.

[21] Appl. No.: 936,163

[22] Filed: Dec. 1, 1986

[51] Int. Cl.$^5$ .................. C07H 21/00; C12P 19/34; C12Q 1/68; G01N 30/02
[52] U.S. Cl. .......................................... 435/6; 435/91; 435/803; 436/17; 536/27; 935/1; 935/19; 935/20; 935/21; 935/9; 935/77
[58] Field of Search ................... 435/6, 803; 436/17; 536/27; 935/1, 19, 20, 21

[56] References Cited

PUBLICATIONS

Osterman, L. A. (1984) *Methods of Protein and Nucleic Acid Research* (Springer-Verlag, Berlin, Germany) pp. 288–297.
Potter, A. A. et al. (1985) Cancer Letter 26, pp. 335–341.
Schleif, R. F. et al. (1981) *Practical Methods in Molecular Biology* (Springer-Verlag, Berlin, Germany) pp. 89–96.
Helms, C., et al. (1985) DNA, 4(1), pp. 39–49.
Schott, H. (1984) J. of Chromatography 284, pp. 409–431.
Colpan, M. et al. (1984) J. of Chromatography 296, pp. 339–353.
*Ion Exchange Chromatography* (published by Pharmacie Fine Chemicals in Sweden by Rahms; Lund, 1982) pp. 10–17.

*Primary Examiner*—Amelia B. Yarbrough
*Assistant Examiner*—Ardin H. Marschel
*Attorney, Agent, or Firm*—Pretty, Schroeder, Brueggemann & Clark

[57] ABSTRACT

The method of this invention is applicable to rapid separation, isolation, and purification of DNA or RNA from biological samples. The DNA/RNA may be in double-stranded or single-stranded form. The method is particularly advantageous for resolving genetic DNA or RNA found in bacteria, virus, and mammalian cells, and for use with samples of human bodily fluids and tissues, including stool, sputum, urine, and blood samples. DNA or RNA can be separated effectively from interfering components, particularly proteins, biological pigments and mucopolysaccharides. The method of the present invention can utilize commercially available strong or weak anion exchanger materials with selected solutions of known ionic strength for adsorption and elution.

28 Claims, No Drawings

METHOD OF ISOLATING AND PURIFYING NUCLEIC ACIDS FROM BIOLOGICAL SAMPLES

FIELD OF INVENTION

The field of this invention relates to the rapid separation, isolation, and purification of nucleic acids, DNA and/or RNA, from biological samples. The method is particularly concerned with the rapid and simple purification of nucleic acids from bodily fluids or tissues for clinical diagnosis using nucleic acid hybridization techniques.

BACKGROUND OF INVENTION

Several procedures for the isolation of DNA or RNA from biological samples have been published. One of the earliest procedures for isolation of bacterial DNA utilized a precipitation with alkyltrimethylammonium bromides; see Jones, *Biochim. Biophys. Acta* (1953) 10:607–612; and Jones, *Nature* (1963), 199: 280–282. In the Jones procedure, the alkyltrimethylammonium bromides also precipitate other components, the salts must be completely removed, and a subsequent series of extractions and precipitations are required to obtain the purified DNA, a procedure which takes 1-2 days. No complex biological samples were used.

A later procedure for isolation of DNA from microorganisms was first described in Marmur, *J. Mol. Biol.* (1961) 3:208–218. The Marmur procedure also involves a series of extractions and precipitations utilizing the caustic reagents phenol and chloroform. Both the Marmur and the Jones procedures use ethanol as a precipitating agent. The Marmur procedure is still considered the state of the art, but requires 1-2 days to perform. Both methods use harsh organic solvents, which additionally make them clinically unacceptable.

From some biological fluids such as urine or blood, other direct and rapid preparation methods are known, such as direct lysing and spotting. For example, see Gillespie, et al., *BioTechniques* Nov./Dec. 174–192 (1983) and Barker et al., *Science* 231:1434–1436 (1986). Also see general techniques described in *Nucleic Acid Hybridization: A Practical Approach*, B. Hanes and S. Higgins, eds., IRL Press, Washingon (1985). As the authors themselves discuss, however, the methods cannot be used directly for clinically relevant sample sizes, for even in these relatively simple samples interference from components other than nucleic acids become unacceptable.

In addition to these extraction/precipitation purification methods, chromatographic column separation procedures have been proposed using several specially designed column packing materials, viz. the "NENSORB 20" cartridges sold by DuPont NEN Products, Boston, Mass., which function primarily by reverse phase adsorption and are not recommended for biological samples, the "NUCLEOGEN" DEAE weak anion exchange materials for HPLC sold by Machery-Nagel, Duren, West Germany; and strong anion exchange materials used for HPLC, such as Whatman Partisil SAX. However, the chromatographic column systems heretofore used are lengthy, require HPLC instrumentation that mandate high pressure to obtain adequate separation and are incapable of isolating nucleic acids from complex biological samples containing many components other than nucleic acids, such as those prepared from feces, blood or other bodily fluids or tissues. Adding such samples to these column systems would cause unavoidable degradation, resolution loss and blockage of the column. As such, in order to make these systems practical for adequate isolation of nucleic acids, significant sample pretreatment is required and mechanical backpressures necessitate the use of sophisticated pumping and delivery systems.

State of the art isolations of DNA/RNA continue to employ a variation of the twenty year old method described by Marmur, which utilizes many tedious and time consuming steps, requires numerous treatments with unacceptable organic solvents and does not provide adequately isolated nucleic acids needed for hybridization assays in a clinical laboratory. Contaminates in the biological samples interfere with fixing DNA/RNA hybridization and detection. As a consequence, to provide useful clinical hybridization assays, there exists a need for rapid methods to obtain hybridization nucleic acids from biological samples. Currently, such a system does not exist. Such methods must be rapid—(1) minutes rather than hours or days; (2) be efficient—can recover sufficient RNA or DNA to detect hybridization; (3) require little or no sample pretreatment; (4) not require expensive instrumentation or pumps; (5) not use organic solvents or vigorous conditions; (6) be essentially universal in nature—can be used for any length RNA or DNA, single or double-stranded; and (7) result in high purity DNA or RNA, thus eliminating background contaminants from the biological material. The present invention fills that need with a novel method combining rapid lysis of samples with subsequent isolation of nucleic acids contained in highly contaminated biological samples by a simplified anion exchange separation.

A laboratory procedure is known in which DNA can be recovered from agarose gels by electrophoresis which separates the DNA from sulfated mucopolysaccharides present in the sample. This procedure recognizes that the mucopolysaccharides usually extract from the sample together with the DNA, and uses this special electrophoresis procedure to separate these components. Following the separation of the DNA from the mucopolysaccharides by electrophoresis, and the DNA fraction is cut out and the DNA electroeluted it is proposed to further purify the gel by passing it through "DEAE-Sephacel". In this procedure the DNA applied to the column is washed with 0.3M aqueous NaCl, and thereafter the DNA is eluted with 0.6M aqueous NaCl. The eluant is extracted twice with phenol, once with phenol/chloroform, and once with chloroform. The DNA is then recovered from the purified eluant by precipitation with ethanol. See Maniatis, et al., "Molecular Cloning" (1982), pages 164–166. Although the above described procedure does separate mucopolysaccharides from the desired DNA, the method is laborious. It involves electrophoresis elution, column separation, and phenol chloroform extraction.

SUMMARY OF INVENTION

The method of this invention is applicable to rapid separation, isolation, and purification of DNA or RNA from biological samples. The DNA/RNA may be in double-stranded or single-stranded form. The method is particularly advantageous for resolving genetic DNA or RNA found in bacteria, virus and mammalian cells and for use with samples of human bodily fluids and tissues, including stool, sputum, urine and blood samples.

Such biological samples contain acid mucopolysaccharides and other contaminating and interfering molecules which are particularly difficult to separate from DNA/RNA by conventionally described procedures. Acid mucopolysaccharides are polymers which contain regularly spaced sugars and anionic charges and as such can closely mimic nucleic acids. In clinical samples requiring examination of DNA/RNA from pathogenic organisms (bacteria or virus), carboxylated and/or sulfated mucopolysaccharides may be present and are known to cause high backgrounds in hybridization assays, and compete in an undesirable manner for binding to membranes, which reduces hybridization results. It is an important feature of the present invention that DNA or RNA can be separated effectively from interfering components, particularly proteins, biological pigments and mucopolysaccharides such as hyaluronic acid, chondroitin, dermatin, heparin, and keratin.

For clinical identification of pathogens, it is desirable to recover the DNA/RNA from bodily fluids, tissues or excretions containing the bacteria/virus. Such samples may be derived, for example, from feces, urine, blood, sputum and wound exudates. All such samples may be highly contaminated with water-soluble components. Stool samples contain bile pigments and other substances in addition to mucopolysaccharides which can produce undesired background fluorescence and adsorbance effects unless removed from the DNA/RNA before hybridization assays. A further important feature of the present invention is that such interfering substances can be readily separated from the DNA/RNA to be analyzed.

The method of the present invention can utilize commercially available anion exchange materials. Either strong or weak anion exchangers may be employed with aqueous solutions. By utilizing selected solutions for adsorpotion and elution, the nucleic acids (DNA or RNA) can be purified, concentrated, and substantially isolated.

By employing a solution at known ionic strength for the initial binding of the nucleic acids to the anion exchange column materials, most of the water soluble components including other electronegative molecules such as proteins (lesser-bound contaminants) can be washed through the column. For elution, the required ionic strength is generated by using known concentrations of a salt such as NaCl, which may be mixed with a buffer to control pH strength, ideally corresponding to the lowest ionic strength at which the nucleic acids will completely elute. Contaminating substances adsorbed under the same conditions as the nucleic acids may thereby be left within the column, i.e., stronger bound contaminants are separated away from the nucleic acids.

In one preferred embodiment, two columns (or column sections) are employed for the isolation of the DNA or RNA. Two beds of different anion exchange materials are used. The first bed in the direction of flow is a weak anion exchanger and the second bed is a strong anion exchanger. A preferred weak exchanger is one in which primary, secondary, or tertiary amine groups (i.e., protonatable amines) provide the exchange sites. The strong base anion exchanger has quaternary ammonium groups (i.e., not protonatable and always positively charged) as the exchange sites. Both exchangers are selected in relation to their respective absorption and elution ionic strengths and/or pH for the DNA or RNA being separated. The solution strengths are higher than the binding strengths.

With a two-bed system, which may be in the form of separate columns or arranged as stacked beds in a single column, the elution condition of the first bed must be an effective binding condition for the second bed. These conditions may be related so that the lowest ionic strength at which all of the nucleic acids can be eluted from the first bed is the ionic strength and/or pH at which substantially all of the nucleic acids will be bound in the second bed.

By limiting the conditions of the eluants to the lowest ionic strength at which all the nucleic acids can be substantially eluted, stronger binding contaminating components such as mucopolysaccharides can be left within the beds. In the two-bed system, the wash solution used to flush unbound components through the first bed can be passed through the second bed. This gives assurance that any nucleic acids which are not immobilized in the first bed will be bound in the second bed.

In preferred embodiments of the method of the present invention, nucleic acids are isolated and purified in aqueous solution samples containing the nucleic acids together with water-soluble components of lysed cells or virus, including carboxylated and/or sulfated mucopolysaccharides. An ion exchange column material is selected which effectively binds the target nucleic acids, such as double-stranded DNA, at a lower salt molarity than the molarity at which the target nucleic acids elute therefrom. A prepared sample is applied to a column packed with a selected anion exchange material, the anionic groups of the column material being in chloride or other anionic form. The nucleic acids become bound to the column material, and the column is then washed with an aqueous solution of a chloride salt at a chloride molarity at which the nucleic acids remain bound to the column material.

To accomplish the purification results of the present invention, which includes particularly the separation of the DNA from acid mucopolysaccharides, the first wash molarity should be close to the lowest chloride molarity at which the nucleic acids begin to elute. This wash is then applied in sufficient volume to wash the nonbinding components through the column, including particularly the carboxylated mucopolysaccharides. The bound nucleic acids are then eluted by passing through the column an aqueous solution of a chloride salt having an eluting chloride molarity corresponding to the lowest chloride molarity at which the nucleic acids will completely elute. This eluant is passed in sufficient volume to remove the nucleic acids from the column while leaving the sulfated mucopolysaccharides and other interfering substances in the column. The eluted nucleic acids are then recovered essentially free of both kinds of mucopolysaccharides, the carboxylic and the sulfated forms, proteins, and other interfering molecules. This is a new and unexpected result which has not heretofore been accomplished by the use of chromatographic column containing anion exchange material.

It was not previously known that there were chloride molarities which can selectively immobilize nucleic acids and sulfated mucopolysaccharides while permitting carboxylated mucopolysaccharides to pass through the column. Nor was it known that there were chloride molarities at which bound nucleic acids could be eluted from a column while leaving sulfated mucopolysaccharides therein. The discovery of the practicality of such differentiating molarities is an important part of the present invention.

DETAILED DESCRIPTION

The primary materials required for practicing this invention are commercial anion exchange column materials, a salt, and a suitable buffer to control pH. The column adsorbents include strong base anion exchangers of the quaternary ammonium type, weak base anion exchangers of the amine type. Preferably the weak base exchangers have tertiary amine exchange sites, although ones having primary amine exchange sites can also be used. Such anion exchanges are supplied as semi-porous, generally spherical or irregular granules of a size adapted for use in chromatographic columns. Suitable granule diameters can range from about 20 μm to 200 μm, and effective pore sizes can range from about 50 Å to several thousand, depending on target DNA/RNA and contaminant size. Commercial materials are available from several manufacturers, including Bio-Rad Chemical, Pierce Chemical Company, Toyo Soda Mfg. Co., and Pharmacia Fine Chemicals. Weak base exchangers can have matrix bases comprising agarose, silica glass, vinyl polymers, etc. The silica glass may be coated, such as "Glycophase" coating, glycerol glass, etc. Tertiary amine groups are commonly diethylaminoethyl, referred to as "DEAE" exchangers. Other tertiary amine groups can be employed. Primary amine groups are commonly in aminoethyl form but other primary or secondary amine groups could be present. Strong base anion exchangers are supplied with a matrix base of silica glass, either uncoated or with a glycophase coating, or with an agarose base. The quaternary groups are usually diethylmethylammonium or trimethylammonium, respectively referred to as "QAE" or "QMA" exchangers.

exchangers can be determined using test substrates of pure DNA or RNA corresponding to the molecular forms of the DNA or RNA of the samples to be tested, comprising the target nucleic acids. In determining the respective binding and elution molarities of the selected anion exchanger, standard chromatographic procedures can be used for detecting adsorption and elution of the test material. For example, the DNA or RNA can be labeled with a suitable marker, permitting solutions to be continuously monitored as they exit the column and/or eluted concentrations may be followed spectrophotometrically.

Typically, pure aqueous solutions (50 mg/ml–250 mg/ml) of the specific target DNA or RNA to be examined are loaded in known amounts on experimental columns in a salt low enough to assure efficient binding. The nucleic acids are then eluted using step or gradient elutions of increasing competing salt concentrations, and all fractions are monitored spectrophotometrically, typically with absorbance at 260 nm, to find the range of molarities where the nucleic acids begin to elute and where they are largely recovered. Subsequently, the measurements are fine-tuned and capacity/recovery measurements are taken. It is advantageous to use a matrix that has a small molarity range between the beginning of elution and full recovery.

The method can effectively be used with gravity flow columns, and this method of column operation is preferred for simplicity.

Binding and elution chloride molarities have been determined for representative commercial anion exchangers using DNA and RNA test materials and aqueous sodium chloride. The discriminating molarities which can be employed in practicing the method of this invention with these anion exchangers are summarized in the following table.

REPRESENTATIVE BINDING AND ELUTION NaCl MOLARITIES
FOR COMMERCIAL ANION EXCHANGERS WITH DNA and RNA SAMPLES

| Commercial Designation | Anionic Group | Matrix Base | Bind (Wash) NaCl/Elute NaCl | | |
|---|---|---|---|---|---|
| | | | dsDNA[5] | ssRNA[6] | dsRNA[7] |
| Affi-Gel 102[1] | primary amine | agarose | 0.3 M/0.5–0.6 M | | |
| DEAE Glycophase[2] | tertiary amine | silica glass | 0.2 M/0.6 M | | |
| Fratogel TSK DEAE 650-S[3] | tertiary amine | vinyl polymer | 0.3 M/0.5 M | 0.1–0.3 M/0.5–0.6 M | |
| DEAE Sepharose CL-6B[4] | tertiary amine | agarose | 0.3 M/0.5–0.6 M | | |
| QAE Glycophase[2] | quaternary ammonium | silica glass | 0.5–0.6 M/0.8 M[8] | 0.5 M/0.7 M | 0.3 M/0.7 M |
| QMA Glycophase[2] | quaternary ammonium | silica glass | 0.5–0.6 M/0.8 M[9] | 0.5 M/0.7 M[9] | |
| QAE Sepharose CL-6B[4] | quaternary ammonium | agarose | 0.5–0.7 M/1.0 M | | |

[1] Bio-Rad Chemical Division, Richmond, CA
[2] Pierce Chemical Company, Rockford, IL 61105
[3] Toyo Soda Mfg. Co., Ltd., Yamaguchi, Japan
[4] Pharmacia Fine Chemicals AB, Uppsala, Sweden
[5] Determined with E. coli double-stranded DNA.
[6] Determined with single-stranded ribosomal RNA.
[7] Determined with double-stranded rotovirus RNA.
[8] Eluant also contained 17% methanol.
[9] Eluant also contained 10% methanol.

The method of the present invention in preferred embodiments utilizes the anion exchange column material in chloride form, and selected critical chloride molarities for applying, washing, and eluting the nucleic acids. The preferred chloride salt is sodium chloride, but the cation of the chloride salt can be varied. Consequently, other alkali metal chlorides such as ammonium and potassium chloride can be used instead of sodium chloride, and although not preferred, the cation may also comprise an ammonium ion or a divalent ion such as magnesium.

The discriminating binding and elution chloride molarities of the selected weak base and/or strong base In the foregoing table, the binding chloride molarities are also the preferred wash molarities. These bind/wash molarties are molarities at which substantially all of the target DNA or RNA is bound but are close to a molarity at which nucleic acids begin to elute. The difference between full binding and beginning elution is at least 0.1M chloride and usually in the range of about 0.1 to 0.3M. The full elution molarities shown in the table are substantially higher than the lowest molarities at which elution begins, comprising the lowest molarities at which complete elution of the nucleic acids be obtained. Higher elution molarities than those shown could be employed. However, increases of more than 0.1 to 0.2M can result in elution of other adsorbed components reducing the purity of the final product.

When a single bed of an anion exchanger is used for the separation, either a quaternary or a tertiary amine exchanger are preferred. Where two beds are employed, the first bed should comprise a weak base anion exchanger, such as the tertiary amine type, and the second bed a strong base quaternary ammonium exchanger. The two beds may be in separate columns or both beds may be stacked within a single column.

In the dual bed embodiment, the molarity employed for elution of the first bed may correspond with a molarity at which the nucleic acids are fully bound in the second bed. For example, with reference to the above table, the "FRACTOGEL" tertiary amine adsorbent could be used as the first bed in combination with a QAE Glycophase quaternary ammonium exchanger as the second bed. As indicated in the above chart, dsDNA elutes the "FRACTOGEL" at 0.5M, which is an effective binding molarity for the QAE exchanger. The wash solution used with the first bed may be passed through the second bed wherein soluble components that were not immobilized in the first bed are retained.

To assure complete elution of the nucleic acids, a small amount of an organic solvent may be added to the eluant solutions. Methanol is preferred for this purpose, but other lower alcohols, including ethanol, propanol and isopropanol, can be used. In general, the amount to be added will range from about 5 to 20% by volume. Other more organic components such as ureas or formamides may also be used. In certain of the eluant solutions tested as shown in table footnotes, methanol was added but such use of methanol is optional. It may, however, assist more complete recovery of the DNA or RNA by reducing undesired binding character of the matrix.

Columns for use in practicing the present invention can be of small size and volume. Typically, for example, bed volumes of from about 0.1 to 10 cubic centimeters (cc) can be used, the beds being contained in columns or cartridges with internal diameters from about 0.3 to 3 centimeters (cm). Small compact cartridges can be prepared for commercial use of the invention. Where the stacked bed system is employed, the volumes of each bed can be the same as those indicated. Although batch processing by suspending the anion exchanger in solution can also be used, flow columns are generally faster and more efficient. A particular embodiment of the invention is optimizing flow properties by the selection of resin mesh sizes and pore sizes allowing for good gravity flow with maximum trapping of contaminants.

The aqueous sodium chloride solutions described above for binding preferably have a pH around neutrality, that is, neither strongly based or acidic. For example, a pH within the range from about 5 to 9 can be used by employing known buffers. In certain embodiments, however, such as may be required for effective pH gradients on DEAE resins, a pH which is more alkaline or acidic may be employed, such as from pH 3 to 13.

Biological materials from which samples can be prepared for use in the method of this invention include but are not limited to bacterial cultures, cells infected with virus, isolated virus, tissue cultures, cell lines and foods contaminated with bacteria. The method is particularly designed for clinical samples to diagnose pathogens. For example, samples can be prepared from feces, blood or serum, urine infected with bacteria, or other bodily excretions such as sputum or wound exudate.

The test sample may be prepared by known procedures as used for lysing cells and/or viruses to obtain aqueous solutions of cellular or viral nucleic acids. Such solutions will contain the nucleic acids together with other water-soluble components of the lysed cells or virus. In the case of bodily fluids or exudates, the samples will usually contain acid mucopolysaccharides. In stool samples, the total nucleic acids present may additionally include nucleic acids from meat or vegetable cells eaten by the patient, and from normal intestinal and stool flora.

Crude substrates are prepared or obtained as aqueous suspensions. For example, the solids of feces may be suspended in an aqueous solution using an ionic strength and/or pH corresponding to that for applying the samples to the column material. Sodium chloride, for example, may be added to the aqueous substrates to achieve the desired molarity. A lysing agent for the cells or virus is added, such as sodium lauryl sulfate or an enzymatic lysing agent. A lysing enzyme, such as Proteinase K may be employed in conjunction with an anionic, nonionic, or zwitterionic detergent. To protect the DNA/RNA, chelating agents may be added, such as ehthylenediaminetetraacetate (EDTA), thereby preventing the nucleases and/or bivalent metal ions from degrading the DNA/RNA. Incubation for short times (5-60 minutes) at controlled temperatures (20°-70° C.) are also useful. After lysing, the solids can be separated by centrifugation or filtration. The supernatant provides the sample for use in the method of the invention. As required, the pH of the sample is adjusted to a more neutral pH. Salts can be added to increase the ionic strength or water can be added to reduce the ionic strength.

Where the specimen is prepared from blood, an anticoagulant should be added. The EDTA used to protect the DNA/RNA against degradation will also perform an anticoagulant function. This is preferred to the addition of heparin, which is an acid mucopolysaccharide and as such can contribute to contaminant backgrounds.

In preparing samples from urine, bacterial cells in the urine may be first collected by centrifugation (pelleting), and then resuspended in lysing reagent.

Cells from culture may be either harvested off plates or collected from broth. If the cells are in glycerol or dimethylsulfoxide (DMSO), the cells may be washed to remove these agents. The pelletized cells may be resuspended and processed as described with respect to bacterial cells in urine.

For virus-infected cells, the virus will usually be inside the cells. When the cells are lysed, the virus will be liberated. The virus DNA or RNA is released by appropriate known conditions. Additives and treatment for preparation of the sample will otherwise be as described. After completion of the lysing, the solids are removed to obtain a supernatant.

The anionic exchangers may be supplied in form for use, or they can be converted to the desired form by passing aqueous salt solution therethrough. For example, a NaCl solution can be used to convert a bed or resin to the chloride form in a column. Alternatively, the exchanger before packing in a column can be soaked in the NaCl solution or cycled in a known manner with HCl and NaOH.

After the column (or series of columns) has been prepared, the clarified solids-free sample is applied to the column. Where a gravity flow system is used, or preferred, the sample may be poured onto the top of the column. The sample as applied may have lower NaCl molarity, such as 0.1M NaCl than used for the binding-/washing step. The sample is washed into the column with aqueous NaCl at the ionic strength and/or pH at which the nucleic acids begin to elute, as described above. The washing volume should be sufficient to wash to lesser-binding components through the column. Usually a wash from 1 to 5 column volumes will be adequate.

The wash is discarded where a single bed is employed and also may be discarded where a second bed is also employed. Preferably, however, if a second bed is utilized, the wash is passed through the second bed.

The bound nucleic acids are eluted by passing through the column or first bed an aqueous eluting solution element having an increased ionic strength, such as preferably a greater chloride molarity, corresponding to the lowest conditions at which the nucleic acids will completely elute. The eluant is passed in sufficient volume to remove the nucleic acids from the column or first bed, usually requiring from about 1 to 5 column volumes of eluant. For single bed embodiments, the nucleic acids are recovered in the eluant. However, the eluant can be further processed, such as by adding precipitating agents for the nucleic acids.

Where two separate beds or a single column stacked bed is employed, the eluant from the first bed is passed through the second bed. The ionic strength of the eluant is an effective binding condition for the second bed, and nucleic acids become bound in the second bed. Additional quantities of aqueous solution may be passed through the second bed or sequentially through the first and second beds to wash out the nonbound components. Usually from about 1 to 5 column volumes will be adequate for this washing step.

Adsorbed nucleic acids in the second bed are eluted by passing through a stacked column or separately through a second bed an aqueous eluant having an eluting chloride molarity higher than that of the first column eluant. The higher molarity preferably corresponds to the lowest chloride molarity at which the nucleic acids are completely eluted from the second bed. This eluant is passed through the column or second bed in sufficient volume to remove the nucleic acids from the column.

In embodiments where the sample containing the target nucleic acids, such as particularly double-stranded DNA, includes carboxylated and sulfated mucopolysaccharides together with other water-soluble components of lysed cells or virus, use of discriminating chloride molarities can effectively separate target nucleic acids from either or both kinds of acid mucopolysaccharides. After the application of the sample to the column, at a chloride molarity at which substantially all of the nucleic acids become bound to the column material, the washing of the column at a critical chloride molarity achieves the separation of the carboxylated mucopolysaccharides. By utilizing as the wash an aqueous solution of a chloride salt at a chloride molarity at which the nucleic acids remain bound to the column material and selected so that the molarity is close to the lowest chloride molarity at which the nucleic acids begin to elute, the column may be washed with sufficient volume of the wash solution to remove the relatively weaker binding components, including particularly the carboxylated mucopolysaccharides. In the next step of the method, the bound nucleic acids are selectively eluted by passing through the column an aqueous solution of a chloride salt having an eluting chloride molarity corresponding to the lowest chloride molarity at which the nucleic acids will elute. This eluant can then be passed through the column in sufficient volume to remove the nucleic acids from the column while leaving sulfated mucopolysaccharides therein. The recovered eluted nucleic acids thereby obtained are essentially free of mucopolysaccharides.

The method of this invention is further illustrated by the following representative examples of the presently preferred modes for practicing the invention.

EXAMPLE I

Isolation and Purification of DNA from Feces Using a Strong Base Anion Exchanger 1. Sample Preparation:

(a) About 1.0 gm of stool (preferably fresh, but may also be refrigerated or frozen to prevent nucleic acid degradation) is added to about 8.0 ml of 0.5M NaCl/0.02M $Na_2EDTA$ in an enclosed tube which may also contain a small amount of inert projectiles which will aid in breaking up large fibrous masses in firmer healthy-type stool when vigorous shaking is used. (Diarrhea stool will not usually require this vigorous step to suspend the microorganisms in the NaCl/EDTA solution).

The test tube is shaken vigorously by hand 3-8 min. as required to break masses. Large debris is then pelleted by gentle centrifugation (5 min. at a low speed in a clinical centrifuge). The soluble supernatent is used in the subsequent lysing procedures and it contains the suspended microorganisms and soluble and small particulate contaminants.

(b) For each column 500 μl of the sample is added to the following:
- 750 μl Proteinase k (@10 mg/ml)
- 100 μl 20% SDS
- 150 μl 8M urea Final volume=1.5 ml
Final concentrations=
0.013M NaCl
0.05M $Na_2EDTA$
5 mg/ml Proteinase K
1.3% SDS
0.8M Urea
plus stool components and salts The sample is now heated to 50°–60° C. in a water bath for 15–20 min. with one intermediate mixing.

The sample is removed and diluted 1:2 with 1.5 ml ion-free water. The stool solution itself is a naturally buffered one and thus no additional buffer is used. pH remains in the 6.5–7.5 range, typically.

2. Column Preparation:

(a) A quaternary ammonium anion exchanger identified in Table A (Pierce QAE Glycophase Glass; 75–125 μm irregular particles, 200 Å pores) is added dry to a flask containing 0.1M NaCl. It is degassed using a vacuum pump or aspirator for 10–15 minutes. It is then loaded into 0.7 cm×10 cm columns, setting up a bed volume of 3.0 ml. Packing is facilitated by applying vibration.

(b) To make certain the matrix is converted to chloride form 15 ml of 2.0M NaCl is passed through the column, followed by 6 ml of $H_2O$, 15 ml of wash solution (0.5M NaCl 17% MeOH) and 15 ml of elute solution (0.8M NaCl 17% MeOH), then rinsed with 6 ml H₂O and equilibrated with 0.5M NaCl 17% MeOH (9 ml). The column is now ready for sample application. Do not let column get dry. (All solution molarities in this and subsequent examples are referenced to aqueous solutions except as otherwise noted.)

3 Purification Procedure:

(a) The prepared sample (3.0 ml) is slowly loaded on the column and flow is by gravity in some instances or by gentle manual application of pressure using a stoppered syringe.

(b) The column is now washed with 5 column volumes of aqueous wash solution (0.5M NaCl; 17% MeOH which may be preceded by 0.5M NaCl wash alone). The polycarboxylated mucopolysaccharides and protein are thus washed through the column while leaving the DNA/RNA bound thereon. The sulfated mucopolysaccharides also remain in the column.

(c) The nucleic acids (DNA) are eluted with 9 ml of aqueous 0.8M NaCl, 17% MeOH and 0.5 ml fractions are collected and analyzed. The yielded nucleic acids are ready directly for whatever the required purpose. The sulfated mucopolysaccharides remain bound in the column. The DNA/RNA thus obtained is essentially free of acid mucopolysaccharides.

4. Analysis:

Typical analysis of the nucleic acids include spectrophotometric scans (210 nm→300 nm), comparison of 260 nm/280 nm absorbance ratios, and 230 nm/260 nm absorbance ratios for purity and concentrate. Agarose gel electrophoresis determines DNA condition (state of intactness) and staining with Stainsall will help confirm the purification away from proteins and acid mucopolysaccharides. Fluorescent scans may be used to detect containment fluorescence, and DNA hybridization tests are done to determine presence of intact target regions of the collected DNA.

5. Results:

By these procedures significant amounts of nucleic acids are isolated and purified from feces and >80% of the isolated nucleic acids may be found concentrated in 1.0-2.0 ml total volume of eluant.

EXAMPLE II

Isolation and Purification of DNA from Feces Using a Weak Base Anion Exchanger

1. Sample Preparation:

The feces sample is prepared as described in Example I.

2. Column Preparation:

A tertiary amine anion exchanger identified in Table A (TSK Fractogel DEAE-650 S) preswollen as 20-50 μm particles is employed. A concentrated amount of the resin is added to a flask containing 0.1M NaCl. It is degassed using a vacuum pump or aspirator for 10-15 minutes, and it is then loaded into 0.7 cm × 4 cm column and a bed of 1.0 ml volume is set up. Packing of these spherical particles may be accomplished by gravity settling (whereas the irregular glass particles of Example I require trapping and or gentle vibrations to set up a good, dense, consistent bed).

(b) The column is next converted as necessary to chloride counterion form by passing 5 column volumes of 2.0M NaCl therethrough, followed by an H₂O rinse of 3 column volumes (3 mls) and an equilibration with 0.3M NaCl at 3 column volumes (3 mls). The column is now ready for sample application. Do not allow column to run dry.

3. Purification Procedure:

(a) The prepared feces sample (see Example 1, 1.a and b, 3.0 ml total volume) is slowly loaded on the column and flow is by gravity or by gentle manual application of pressure using a stoppered syringe.

(b) The column is now washed with 15 column volumes (15 ml) of 0.3M NaCl. The polycarboxylated mucopolysaccharides are washed through the column and the DNA/RNA remains bound.

(c) The column is then eluted with 3 column volumes (3 ml) of 0.5 M NaCl. If fractions are collected one will usually find that greater than 80% of the recovered nucleic acids are found in a volume of about 1.0 ml. The eluted DNA is directly ready for whatever the required purpose. The sulfated mucopolysaccharides remain bound in the column.

4. Analysis:

The analysis is the same as Example I, 4. The DNA/RNA is obtained essentially free of acid mucopolysaccharides.

EXAMPLE III

Isolation and Purification of DNA from Feces Using a Stacked Column System Composed of Both a Weak and a Strong Base Anion Exchanger 1. Sample Preparation:

The sample preparation is the same as described in Example I, 1a and b.

2. Column Preparation:

The tertiary amine and quaternary ammonium exchanger used are the same as described in Examples I and II. This preparation is essentially the same as for Example I 2.a), and Example II 2.a). The strong base glass exchanger is loaded first in the 0.7 cm × 10 cm columns and packed with vibration to a 2.0 ml volume height. Then a polyethylene column disc is placed on the bed top, followed by application of the weak base Fractogel which is gravity packed to a 1.0 ml bed height (3.0 ml volume column total).

(b) 5.0 column volumes (15 ml) of 2.0M NaCl is passed through the composite column for ion conversion, followed by 6 ml H₂O, 5.0 column volumes of 0.5M NaCl 17% MeOH, (15 Ml) and 15 ml of 0.8M NaCl 17% MeOH), then 6 ml H₂O, and final equilibration with 9 ml (3 volumes) of 0.3M NaCl. The column is now ready for use.

3. Purification Procedure:

The procedure is similar to Examples I and II except as follows: After the sample is loaded, the column is washed with 5 column volumes (15 ml) of aqueous 0.3M NaCl. The nucleic acids are now bound in the upper weaker base column (Fractogel). The DNA is now eluted from the upper column into the lower one (strong base Glycophase glass) by application of 5.0 column volumes (15 ml) of 0.5M NaCl, 17% MeOH, which also serves as a wash for the lower column. Finally, the DNA/ RNA is eluted from the lower column with 3.0 column volumes (9.0 ml) of 0.8M NaCl 17% Moore. Analysis of the fractions should confirm that the nucleic acids are concentrated into a 1.0-2.0 ml volume. The recovery of nucleic acids is increased and their purity even higher than in Examples I and II.

EXAMPLE IV

Isolation and Purification of Nucleic Acids Contained in Whole Blood Samples

1. Sample Preparation:

(a) Fresh blood is collected in blood collecting vials containing anticoagulant EDTA ($K_3$) (25 mM final concentration). The following mixture is then prepared:

| |
|---|
| 250 µl blood solution |
| 250 µl 0.1 × SSC (=15 mM NaCl 1.5 mM Na Citrate) |
| 500 µl Proteinase K (@ 10 mg/ml) |
| 100 µl 1% SDS |
| 1,100 µl total |

(b) The solution is incubated at 50° C. for 10-20 minutes, with an intermediate gentle mixing. The mixture experiences cleaning and turns a clear-dark brown. A high speed 2. Column Preparations:

The column preparation can be the same as described in Examples I, II or III.

3. Purification Procedures:

The purification procedures can be the same as described in Examples I, II or III.

4. Analysis:

The analytical procedures can be the same as described in Example I.

5. Results:

This whole blood screening will collect nucleic acids from both the blood cells and the pathogens (if present), either inside or outside of the blood cells. If the target nucleic acid is known to exist solely in cells or extracellularly, i.e., buffy coat lymphocytes, appropriate blood fractionating techniques may be used to first isolate these target containing components, and thereafter utilize the method of this invention. For example, the bacteria may be pelletized using a DuPont Isolator 10 microbial tube. Purified RNA/DNA essentially free of acid mucopolysaccharides are obtained.

EXAMPLE V

Isolation and Purification of Nucleic Acids from Infected Urine Samples

1. Sample Preparation:

(a) Infected urine may be thought of as a cell culture broth. A preferred method is to first collect the cells by centrifugation, which greatly concentrates and removes large amounts of contaminants. The cells may then be suspended and lysed as a typical cell culture lysis. For example, pelleted cells may be suspended in 500 µl 0.3M NaCl, with 160 µl 0.25M Na₂EDTA, 80 µl 1.0% SDS, and 250 µl of Proteinase K (@10 mg/ml). The solution is then heated to 50° C. for 10-20 minutes in a water bath.

(b) If desired, it is also possible to screen the whole urine without first pelleting and concentrating the cells. Simply add 250 µl of 0.3M NaCl 0.2M Na₂ EDTA, 500 µl Proteinase K (@10 mg/ml) and 100 µl of 1% SDS to 250 µl of urine, incubate the solution 10-20 minutes at 50° C.

All further procedural information is given in Examples I, II and/or III. The purified nucleic acids are obtained essentially free of acid mucopolysaccharides.

EXAMPLE VI

Isolation and Purification of Nucleic Acids (DNA) Using NaOH as a Primary Cell/Virus Lysing Agent 1 Sample Preparation:

This NaOH procedure can be tailored to any of the samples described above and others. NaOH lysis should be be used for collection of DNA, since basic conditions destroy RNA. Glass column matrices such as glycophase QAE are harmed by basic conditions. The NaOH lysed sample should therefore be neutralized before column application.

Typically, stool, urine, or blood is suspended or mixed with NaCl, EDTA, and NaOH to concentratins of 0.1M, and 0.5M respectively. This brings the pH to near =13 which facilitates lysis. A room temperature incubation of 5-20 minutes is followed by a neutralization, to = pH 8.0 with 500 µl 0.5M Tris Acetate (1.0 ml final volume).

Further procedural information is as described in Examples I, II and/or III.

EXAMPLE VII

Isolation and Purification of Nucleic Acids Using Urea or Other Chaotropic Agents as the Primary Lysing Agent of Pathogens Contained in Samples 1. Sample Preparation:

This example follows directly with Example VI. Stool, urine, or other sample may be used. For simplicity, let's say we have collected cells from urine. The cells may be suspended and lysed in 200 µl 8 M urea, which may be aided with heat if necessary (50° C.), for 5-20 min. The cleared lysate may be quickly microfuged to remove fine particulates, and then loaded directly on a column, prepared as in Examples I-III.

Further procedural information is as described in Examples I, II and/or III.

The conditions set out in the foregoing Examples I to V and VII relate especially to DNA isolation and purification. However, essentially similar procedures can be used for isolation and purification of RNA from the same kinds of highly contaminated biological samples, except that the NaOH lysis procedure of Example VI should not be for RNA isolations. The precise NaCl molarities to be used for optimum purification may require adjustment but this can be easily accomplished. The appropriate load/wash/elute molarities can be readily determined based on the principles of this invention.

Similarly, if another alkali metal chloride as ammonium chloride is substituted for NaCl, the required molarities to accomplish the objects of this invention can be predetermined and adjusted as required for optimum DNA/RNA purification.

EXAMPLE VIII

E. coli DNA is suspended in 0.2m NaCl and added to the column. The column is washed with aliquots of 0.3M sodium chloride, 0.4m sodium chloride. At these concentrations no DNA is eluted. Using 0.5m NaCl the DNA is eluted. When KCl is substituted for the NaCl the same elution pattern is observed. When the E. coli DNA is suspended in 0.2 NH4Cl and applied to the column, the DNA is again eluted with 0.5M NH4Cl.

It will be apparent to those skilled in the art that the method of this invention is susceptible to modifications while still employing the principles of the invention. While as described above the anion exchange column material is preferably in the chloride form, the chloride salts of increasing molarity are employed for the adsorption, washing, and elution other halide salts can be employed, such as bromide or iodide salts. For example, sodium or potassium bromide or iodide can be used in the same manner as described for sodium chloride, with the column being in the same anion form as the salt, that is, in bromide form with bromide salts, in iodide form with iodide salts, etc.

We claim:

1. The method of isolating and purifying cellular or viral nucleic acids from an aqueous solution of a biological sample containing nuclein acids together with water-soluble contamination components of lysed cells or virus selected from the group consisting of proteins, pigments, carboxylated mucopolysaccharides, sulfated mucopolysaccharides, and mixtures thereof, comprising:
   (a) selecting an anion exchange column material which effectively binds the target nucleic acids at a lower salt molarity than the molarity at which the target nucleic acids elute therefrom;
   (b) applying a sample containing nucleic acids together with water-soluble contaminating components of lysed cells or virus selected from the group consisting of proteins, pigments, carboxylated mucopolysaccharides, sulfated mucopolysaccharides, and mixtures thereof, to a column packed with the selected anion exchanger material, and said nucleic acids becoming bound to said column material;
   (c) washing said column with an aqueous solution of a salt at chloride molarity at which the nucleic acids remain bound to said column material, said wash molarity being close to the lowest molarity at which the nucleic acids begin to elute, said washing being of sufficient volume to wash the non-binding components through said column, including carboxylated mucopolysaccharides;
   (d) eluting the bound nucleic acids by passing through said column an aqueous solution of a salt having an eluting molarity corresponding to the lowest molarity at which the target nucleic acids will completely elute, said eluant being passed in sufficient volume to remove said nucleic acids from the column while leaving contaminating components including sulfated mucopolysaccharides in the column; and
   (e) recovering the eluted nucleic acids essentially free of mucopolysaccharides and other contaminating components.

2. The method of claim 1 in which nucleic acids are selected from the group consisting of double-stranded DNA and RNA.

3. The method of claim 1 in which said nucleic acids are selected from the group consisting of single-stranded DNA and RNA.

4. The method of claim 1 in which said sample has been prepared from a bodily fluid or excretion requiring examination for pathogens.

5. The method of claim 1 in which said sample has been prepared from feces.

6. The method of claim 1 in which said sample has been prepared from blood.

7. The method of claim 1 in which said sample has been prepared from sputum.

8. The method of claim 1 in which said anion exchange material contains tertiary amine groups as the exchange sites thereof.

9. The method of claim 1 in which said anion exchange material contains quaternary ammonium groups as the exchange sites thereof.

10. The method of claim 1 in which said washing and eluting solution are passed through said column by gravity flow.

11. The method of isolating microbial double-stranded nucleic acids from an aqueous solution prepared from a body fluid or excretion requiring examination for pathogenic microorganisms, said solution containing water-soluble contaminating components of the body fluid or excretion, selected from the group consisting of proteins, pigments, carboxylated mucopolysaccharides, sulfated mucopolysaccharides, and mixtures thereof, comprising:
   (a) selecting an anion exchange column material which effectively binds the microbial nucleic acids at a lower sodium chloride molarity than the molarity at which the nucleic acids elute therefrom;
   (b) applying a sample containing nucleic acids together with water-soluble contaminating components of body fluid or excretion selected from the group consisting of proteins, pigments, carboxylated mucopolysaccharides, sulfated mucopolysaccharides, and mixtures thereof, to a column packed with the selected anion exchange material, the anionic groups of said column material being in chloride form and said nucleic acids becoming bound to said column material;
   (c) washing said column with aqueous NaCl at a chloride molarity at which the nucleic acids remain bound to the column material, said wash molarity being close to the lowest chloride molarity at which the nucleic acids begin to elute, said washing being of sufficient volume to wash the carboxylated mucopolysaccharides out of said column together with other contaminating components;
   (d) eluting the bound nucleic acids by passing through said column an aqueous NaCl solution having a chloride molarity corresponding to the lowest chloride molarity at which said nucleic acids completely elute without elution of any other mucopolysaccharides which may be present, said eluant being passed in sufficient volume to remove the nucleic acids from said column; and
   (e) recovering the separated nucleic acids essentially free of mucopolysaccharides and other contaminating components.

12. The method of claim 11 in which said mucopolysaccharides include both carboxylated and sulfated mucopolysaccharides.

13. The method of claim 11 in which said washing and eluting solutions are passed through said column by gravity flow.

14. The method of claim 11 in which said sample is prepared from feces.

15. The method of claim 11 in which said sample is prepared from urine.

16. The method of claim 11 in which said sample is prepared from blood.

17. The method of claim 11 in which said sample is prepared from sputum.

18. The method of claim 11 in which said anion exchange material contains tertiary amine groups as the exchange sites thereof.

19. The method of claim 11 in which said anion exchange material contains quaternary ammonium groups as the exchange sites thereof.

20. The method of isolating and purifying cellular or viral nucleic acids from an aqueous solution sample contaminating components of lysed cells or virus selected from the group consisting of proteins, pigments, carboxylated mucopolysaccharides, sulfated mucopolysaccharides, and mixtures thereof, comprising:
 (a) selecting a first ion exchange column material comprising a weak base anion exchanger which effectively binds the target nucleic acids at a lower aqueous chloride salt molarity than the molarity at which the target nucleic acids elute therefrom;
 (b) selecting a second ion exchange material which comprises a strong base anion exchanger which effectively binds the target nucleic acids at a lower aqueous chloride salt molarity than the molarity at which the target nucleic acids elute therefrom, said binding molarity of the second column material corresponding to said eluting molarity of the first column material;
 (c) preparing first and second columns either as separate or stacked columns respectively packed with said first and second column materials in chloride form;
 (d) applying a sample containing nucleic acids together with water-soluble contaminating components of lysed cells or virus selected from the group consisting of proteins, pigments, carboxylated mucopolysaccharides, sulfated mucopolysaccharides, and mixtures thereof, to the first column containing said weak base exchanger, said target nucleic acids becoming bound to the first column material;
 (e) washing said first column with an aqueous solution of a chloride salt at a chloride molarity at which the nucleic acids remain bound to said first column material, said was molarity being close to a chloride molarity at which said nucleic acids begin to elute, said washing being sufficient to wash the nonbinding components through said first column including any carboxylated mucopolysaccharides;
 (f) eluting the bound nucleic acids by passing through said first column an aqueous solution of a chloride salt having an eluting chloride molarity corresponding to the lowest chloride molarity at which the target nucleic acid beings to elute, said eluant being passed in sufficient volume to remove said nucleic acids from said first column while leaving any sulfated mucopolysaccharides therein;
 (g) passing the eluant from said first column through said second column, the nucleic acids eluted from said first column material becoming bound to said second column material;
 (h) eluting the bound nucleic acid from said second material by passing through said second column an aqueous solution of a chloride salt having an eluting chloride molarity higher than that of the first column eluant, which higher molarity corresponds to the lowest chloride molarity at which said nucleic acids will completely elute from said second material, said eluant being passed through said second column in sufficient volume to remove said nucleic acids from said second column; and
 (i) recovering the purified and isolated nucleic acids essentially free of mucopolysaccharides and other contaminating components.

21. The method of claim 20 in which both of said columns are operated under gravity flow, and the wash of step (d) is passed through said second column.

22. The method of claim 20 in which said mucopolysaccharides include both carboxylated and sulfated mucopolysaccharides, said carboxylated mucopolysaccharides being washed through both of said columns, and said sulfated mucopolysaccharides remaining in either said first or second columns after said nucleic acids are removed from said second column.

23. The method of claim 20 in which said sample is prepared from a bodily excretion or fluid selected from the group consisting of feces, blood, urine, and sputum.

24. The method of claim 20 in which said sample is prepared from feces.

25. The method of claim 20 in which said sample is prepared from sputum.

26. The method of claim 20 in which said first material has tertiary amine groups and said second material has quaternary ammonium groups as their anionic exchange sites.

27. The method of claim 20 in which said nucleic acids are selected from the group consisting of double-stranded DNA and RNA.

28. The method of claim 20 in which said nucleic acids are selected from the group consisting of single-stranded DNA and RNA.

* * * * *

UNITED STATES PATENT AND TRADEMARK OFFICE
CERTIFICATE OF CORRECTION

PATENT NO. : 4,935,342

DATED : June 19, 1990

INVENTOR(S) : SELIGSON ET AL.

It is certified that error appears in the above-identified patent and that said Letters Patent is hereby corrected as shown below:

In column 15, line 27, delete "nuclein" and insert therefor --nucleic--.

In column 17, line 19, after sample and before contaminating, insert --containing the nucleic acids together with water-soluble--.

Signed and Sealed this

Twenty-ninth Day of October, 1991

Attest:

HARRY F. MANBECK, JR.

*Attesting Officer*     *Commissioner of Patents and Trademarks*